United States Patent
Wetzig et al.

(10) Patent No.: US 11,852,562 B2
(45) Date of Patent: Dec. 26, 2023

(54) SNIFFING LEAK DETECTOR WITH SWITCHING VALVE AND BUFFER CHAMBER

(71) Applicant: INFICON GmbH, Cologne (DE)

(72) Inventors: Daniel Wetzig, Cologne (DE); Marcel Ruth, Cologne (DE)

(73) Assignee: INFICON GmbH, Cologne (DE)

( * ) Notice: Subject to any disclaimer, the term of this patent is extended or adjusted under 35 U.S.C. 154(b) by 492 days.

(21) Appl. No.: 17/053,442

(22) PCT Filed: May 6, 2019

(86) PCT No.: PCT/EP2019/061540
§ 371 (c)(1),
(2) Date: Nov. 6, 2020

(87) PCT Pub. No.: WO2019/215080
PCT Pub. Date: Nov. 14, 2019

(65) Prior Publication Data
US 2021/0231517 A1    Jul. 29, 2021

(30) Foreign Application Priority Data
May 7, 2018   (EP) .................................... 18171080

(51) Int. Cl.
*G01M 3/04* (2006.01)
*G01N 1/24* (2006.01)
*G01N 33/00* (2006.01)

(52) U.S. Cl.
CPC ............... *G01M 3/04* (2013.01); *G01N 1/24* (2013.01); *G01N 33/0026* (2013.01)

(58) Field of Classification Search
CPC .......... G01M 3/04; G01M 3/20; G01M 3/202; G01M 3/205; G01M 3/38; G01M 3/02;
(Continued)

(56) References Cited

U.S. PATENT DOCUMENTS 3,187,558 A * 6/1965 Koncen ................ G01N 27/185
327/1
3,471,746 A * 10/1969 Roberts .................... G01M 3/20
436/124
(Continued)

FOREIGN PATENT DOCUMENTS

CN     101939628 A     1/2011
CN     104884923 A     9/2015
(Continued)

*Primary Examiner* — David A. Rogers
(74) *Attorney, Agent, or Firm* — The Webb Law Firm

(57) ABSTRACT

Sniffing leak detector including a handheld device with a sniffer tip probe including a sample gas inlet, a reference gas inlet, a gas analyzer, and a switching valve adapted to alternatingly connect the sample gas inlet to the gas analyzer and the reference gas inlet to the gas analyzer in a gas conducting manner, such that either the gas drawn through the sample gas inlet or the gas drawn through the reference gas inlet is analyzed by the gas analyzer, characterized in that the reference gas inlet is arranged in a remote distance from the sniffer tip probe and a reference gas conduit connecting the reference gas inlet and the switching valve includes a buffer chamber adapted to homogeneously mix gas drawn into the buffer chamber through the reference gas inlet with the remaining gas in the buffer chamber.

12 Claims, 2 Drawing Sheets

(58) Field of Classification Search
CPC .......... G01M 3/26; G01M 3/042; G01M 3/06;
G01M 3/12; G01M 3/16; G01M 3/207;
G01M 3/22
USPC ...................................................... 73/40–49.8
See application file for complete search history.

(56) References Cited

U.S. PATENT DOCUMENTS

| | | | | |
|---|---|---|---|---|
| 3,645,127 | A * | 2/1972 | Mongodin | G01M 3/202 73/40.7 |
| 4,167,665 | A * | 9/1979 | Johns | G01N 21/33 250/252.1 |
| 4,393,304 | A * | 7/1983 | Ishida | G01N 33/0026 73/863.44 |
| 4,517,461 | A * | 5/1985 | Crandall | B01D 59/44 250/281 |
| 5,258,050 | A | 11/1993 | Danielson | |
| 5,297,419 | A * | 3/1994 | Richardson | G01N 27/18 422/90 |
| 6,004,514 | A * | 12/1999 | Hikosaka | G01N 30/88 422/89 |
| 6,085,576 | A * | 7/2000 | Sunshine | G01N 33/0031 340/634 |
| 6,635,875 | B1 * | 10/2003 | Bley | G01M 3/38 250/343 |
| 7,010,445 | B2 * | 3/2006 | Battenberg | G01P 3/36 702/77 |
| 7,030,381 | B2 * | 4/2006 | Kilian | G01N 21/3504 250/343 |
| 7,118,919 | B2 * | 10/2006 | Yatscoff | A61K 51/1206 435/14 |
| 7,159,445 | B2 * | 1/2007 | Bohm | G01M 3/205 73/31.03 |
| 7,540,183 | B2 * | 6/2009 | Komninos | G01M 3/24 73/40.5 A |
| 8,176,770 | B2 * | 5/2012 | Wetzig | G01M 3/205 73/40.7 |
| 8,528,386 | B2 * | 9/2013 | Grosse-Bley | G01M 3/202 73/40.7 |
| 8,555,701 | B1 * | 10/2013 | Sacerio | G01N 27/14 73/31.06 |
| 8,826,723 | B2 * | 9/2014 | Henry | G01N 33/0001 73/23.34 |
| 9,021,866 | B2 * | 5/2015 | Takano | G01M 3/18 73/40.7 |
| 9,222,920 | B2 * | 12/2015 | Hirano | G01N 30/0005 |
| 10,168,316 | B2 * | 1/2019 | Ma | G01N 33/0029 |
| 10,309,943 | B2 * | 6/2019 | Hellgren | G01N 33/0062 |
| 10,866,225 | B2 * | 12/2020 | Hellgren | G01N 21/276 |
| 10,935,453 | B2 * | 3/2021 | Wetzig | G01M 3/229 |
| 11,022,515 | B2 * | 6/2021 | Decker | G01M 3/205 |
| 11,181,435 | B2 * | 11/2021 | Jourdan | G01M 3/20 |
| 11,441,969 | B2 * | 9/2022 | Ruth | G01M 3/207 |
| 2003/0209077 | A1 * | 11/2003 | Battenberg | G01P 3/36 73/579 |
| 2004/0051043 | A1 * | 3/2004 | Kilian | G01N 33/0026 250/341.5 |
| 2004/0194533 | A1 | 10/2004 | Bohm et al. | |
| 2006/0150707 | A1 * | 7/2006 | Rolff | G01M 3/207 73/1.05 |
| 2008/0006080 | A1 * | 1/2008 | Wetzig | G01M 3/205 73/40.7 |
| 2009/0212960 | A1 | 8/2009 | Rolff et al. | |
| 2009/0277250 | A1 | 11/2009 | Wetzig | |
| 2010/0313634 | A1 * | 12/2010 | Wetzig | G01M 3/226 73/40.7 |
| 2010/0326169 | A1 | 12/2010 | Grosse-Bley et al. | |
| 2011/0100097 | A1 * | 5/2011 | Gerdau | G01M 3/202 73/40.7 |
| 2013/0276517 | A1 * | 10/2013 | Takano | G01M 3/16 73/40.5 R |
| 2014/0096595 | A1 * | 4/2014 | Wetzig | G01M 3/20 73/40.7 |
| 2015/0308916 | A1 | 10/2015 | Nelles | |
| 2016/0116365 | A1 * | 4/2016 | Luedolph | G01M 3/20 73/40.7 |
| 2016/0223424 | A1 * | 8/2016 | Hilgers | G01M 3/205 |
| 2018/0275010 | A1 * | 9/2018 | Wetzig | G01M 3/226 |
| 2019/0212221 | A1 * | 7/2019 | Decker | G01M 3/205 |
| 2022/0291071 | A1 * | 9/2022 | Coulomb | G01M 3/20 |

FOREIGN PATENT DOCUMENTS

| | | | |
|---|---|---|---|
| DE | 10133567 A1 | 1/2003 | |
| DE | 10316332 A1 | 11/2004 | |
| DE | 102006056215 A1 | 6/2008 | |
| DE | 102013219464 A1 * | 3/2015 | ............... F04F 5/22 |
| EP | 2270457 A1 | 1/2011 | |
| JP | 3882612 B2 * | 2/2007 | |
| WO | 0248686 A2 | 6/2002 | |
| WO | 2009098302 A1 | 8/2009 | |

* cited by examiner

SNIFFING LEAK DETECTOR WITH SWITCHING VALVE AND BUFFER CHAMBER

CROSS-REFERENCE TO RELATED APPLICATIONS

This application is the United States national phase of International Application No. PCT/EP2019/061540 filed May 6, 2019, and claims priority to European Patent Application No. 18171080.7 filed May 7, 2018, the disclosures of which are hereby incorporated by reference in their entirety.

BACKGROUND OF THE INVENTION

Field of the Invention

The disclosure refers to a sniffing leak detector used for the detection of gas leaks.

Description of Related Art

Sniffer leak detection, as described in WO 02/48686 A2, is a method of gas detection. Sniffing leak detectors utilizing gas modulation technique typically comprise a sample gas inlet, through which the gas to be analyzed (sample gas) is sucked, as well as a reference gas inlet through which gas from the surrounding atmosphere (reference gas) is sucked in as a reference for comparison. The gas inflow is a result of a pressure difference typically caused by a vacuum pump within the sniffing leak detector.

WO 02/48686 A2 and WO 2009/098302 A1 disclose to locate the sample gas inlet and the reference gas inlet both on the distal tip of the sniffer tip probe which itself is part of a hand held device (hand piece) to operate the sniffing leak detector.

The gas modulation valve connects the sample gas inlet and the reference gas inlet to a gas analyzer. The sample gas inlet is connected to the gas modulation valve via a sample gas conduit. The reference gas inlet is connected to the gas analyzer via a reference gas conduit. The switching valve switches between the sample gas conduit and the reference gas conduit and thereby connects either of the sample gas inlet and the reference gas inlet to the gas analyzer. Thereby, the gas analyzer is provided with the gas being sucked in through either the sample gas inlet or the reference gas inlet, depending on the switching state of the gas modulation valve.

As described in WO 02/48686 A2, the gas analyzer may be an infrared gas analyzer having a sample cuvette comprising an inlet through which the gas to be analyzed is sucked in, and an outlet for discharging the gas out of the cuvette. An infrared light source and an infrared detector are located on opposing sides of the cuvette, such that the infrared radiation is radiated through the gas contained within the cuvette.

The sniffer leak detectors of the above described type are specially adapted to achieve a high sensitivity. The switching between the sample gas inlet and the reference gas inlet occurs in order to subtract the amount of target gas which is present in the reference gas in the surrounding atmosphere, from the measurement signal obtained from the sample gas. The target gas is the gas which is to be identified within the gas sample, e.g. the gas escaping through a possible leak which is to be detected.

In sniffing leak detection, it is not only desirable to provide for a high sensitivity in order to be able to identify small amounts of target gas within a gas sample. In addition, it is also desirable to allow for a quick orientation within a large area where a leak is assumed to be present. In other words, it is desirable to achieve a signal allowing for a fast and rough assessment or estimation of the direction and distance of an assumed leak in relation to the sniffer tip probe or in relation to the operator of the sniffing leak detector. In general, this is not sufficiently possible by increasing the sensitivity of the sniffing leak detectors.

The object of the disclosure is to provide a sniffing leak detector which allows a fast assessment of the relative direction and/or distance of an assumed leak in relation to the sniffing leak detector or its operator.

SUMMARY OF THE INVENTION

Accordingly, the sniffing leak detector comprises a hand held device with a sniffer tip probe which comprises the sample gas inlet. The sniffing leak detector further comprises a reference gas inlet, a gas analyzer and a switching valve adapted to alternatingly connect the sample gas inlet to the gas analyzer and the reference gas inlet to the gas analyzer in a gas conducting manner, such that either the gas drawn through the sample gas inlet or the gas drawn through the reference gas inlet is conducted to and analyzed by the gas analyzer.

The sniffing leak detector of the disclosure is characterized in that the reference gas inlet is arranged in a remote distance from the sniffer tip probe. This means, that the reference gas inlet is not arranged on the sniffer tip probe. Thereby, a larger distance between the sample gas inlet and the reference gas inlet as compared to the above described prior art sniffing leak detectors is achieved. In addition, a reference gas line which connects the reference gas inlet and the switching valve comprises a buffer chamber circumscribing a buffer volume. The buffer chamber is adapted to homogenously mix gas drawn into the buffer chamber through the reference gas inlet with remaining gas in the buffer chamber. Remaining gas means gas which is already present within the buffer chamber when the gas drawn in through the reference gas inlet enters the buffer chamber.

The effect of the above described characterizing features is that the amount of tar-get gas present in the reference gas is considerably lower than the amount of target gas present in the sample gas, provided that the sample gas inlet is closer to a leak to be detected than the reference gas inlet. This is due to the larger distance between the reference gas inlet and the sample gas inlet as compared to the above described prior art sniffing leak detectors, where the sample gas inlet and the reference gas inlet are close to each other and both located on the sniffer tip. In addition, the buffer chamber provides a low-pass filter for the single component resulting from the amount of target gas present in the reference gas, because the amount of target gas in the reference gas is averaged over time due to the mixing within the buffer chamber. The mixing within the buffer chamber achieves a homogenous gas mixture being analyzed by the gas analyzer. If short pulses or small amounts of target gas are sucked in through the reference gas inlet, these small amounts will be diluted within the buffer chamber, and only the diluted gas mixture is analyzed, rather than a larger amount of target gas present during a short amount of time.

As a result, the homogenous reference gas signal obtained from a remote location as compared to the location from which the sample gas signal is obtained, allows to assess the relative orientation of a leak through which target gas escapes. This can be done by comparing the amount of target gas present in the sample gas with the amount of target gas present in the homogenized reference gas. For example, if the amounts of target gas in the sample gas and in the reference gas are equal, this could be used as an indication that the distance from the sample gas inlet to the leak is the same as the distance from the reference gas inlet to the leak. If the amount of target gas in the reference gas is larger than the amount of target gas in the sample gas, this could be used as an indication that the reference gas inlet is closer to the leak than the sample gas inlet, and vice versa. When switching back and forth between the reference gas inlet and the sample gas inlet, the operator of the sniffing leak detector could quickly achieve an information relating to the relative orientation of a leak with regard to the sniffing leak detector or the sniffer tip probe.

In other words, a large distance between two points of measurement, e.g. between the sample gas inlet and the reference gas inlet, allows for a higher resolution in locating a leak in a three-dimensional space. If the two points of measurement are located next to each other, such as in the prior art sniffing leak detectors, the relative orientation of the leak cannot be assessed. Further, the buffer chamber stabilizes the target gas concentration within the reference gas by homogenous mixing of the reference gas. Functionally, this is a low-pass filter in the time domain for the detection of target gas and therefore eliminates local fluctuation.

A vacuum pump may be employed for continuous suctioning of gas through either of the sample gas inlet and the reference gas inlet, and through the gas analyzer, in order to allow for a continuous influx of gas which permits a real-time assessment of the relative orientation of a leak to be detected while the operator walks through an area where a leak is assumed, such as a large room or space.

Gas is drawn in through the reference gas inlet at a certain volume flow. Preferably, the ratio of the buffer volume within the buffer chamber and the volume flow per second of the gas drawn through the reference gas inlet is at least 1 and at maximum 10000. For example, the volume flow can typically be 1 sccs (standard cubic centimeter per second) while the buffer volume ranges between 1 ccm (cubic centimeter) and 10 liters.

Thereby, an advantageous dilution of target gas present in the reference gas is achieved upon mixing of the reference gas within the buffer chamber.

The buffer chamber may comprise a buffer chamber inlet which is connected to the reference gas inlet, and a buffer chamber outlet being connected to the switching valve. The buffer chamber outlet should preferably be off-set to the buffer chamber inlet with regard to the main gas flow direction through the buffer chamber inlet. This achieves to avoid that the gas entering the buffer chamber through the buffer chamber inlet directly escapes through the buffer chamber outlet without being sufficiently mixed within the buffer chamber. An off-set of the buffer chamber inlet and the buffer chamber outlet with regard to the main gas flow direction through the buffer chamber inlet permits to mix reference gas entering the buffer chamber through the buffer chamber inlet with gas which is already present within the buffer chamber, before the gas escapes through the buffer chamber outlet.

A swirling mechanism is preferably adapted to cause turbulences in the gas stream entering the buffer chamber through the reference gas inlet and through the buffer chamber inlet. This increases the mixing and homogenization of the gas and, thereby, improves the dilution of possible target gas or disturbing gas present in the reference gas.

The swirling mechanism can be of a passive type, such as fins or blades. Alternatively or in addition, the swirling mechanism can be of an active type, such as an actively powered fan or rotor.

An absorber may be provided through which the gas entering the sniffing leak detector through the reference gas inlet is passed, in order to stabilize and homogenize the test gas concentration within the reference gas even further. The absorber may be provided within the reference gas conduit or within the buffer chamber.

Several alternative embodiments are possible for the buffer chamber. In one embodiment, where the sniffer tip probe is located and operated in a room where a leak is assumed, the buffer chamber may be formed by another room within the same building and adjacent to the room where the sniffer tip probe is arranged. In this embodiment, a wall separating the two adjacent rooms comprises the reference gas inlet, such as in the form of an opening or a slit below a door connecting the two rooms.

In an alternative embodiment, the buffer chamber may be adapted to be carried by a user of the sniffing leak detector. The buffer chamber is a separate component compared to the hand held device and comprises a housing to be carried by the operator, such as in the form of a gas bottle comprising the reference gas inlet. In this embodiment, the buffer chamber or its housing comprises the reference gas inlet in the form of an opening to the atmosphere surrounding the buffer chamber. The buffer chamber inlet and the reference gas inlet can then be the same.

In a further alternative embodiment, the buffer chamber may be part of the hand held device. The hand held device may, for example, comprise a housing which also contains the buffer chamber. This housing should then have an opening connecting the buffer volume and the atmosphere surrounding the hand held device, thereby forming the reference gas inlet and the buffer chamber inlet.

A gas outlet may connect the gas analyzer to the open atmosphere surrounding the sniffing leak detector in order to allow for a constant gas flow through the sample gas inlet and the reference gas inlet and through the gas analyzer which is discharged to the open atmosphere through the gas outlet. The gas outlet should be arranged such that the gas blown out through the outlet into the surrounding atmosphere is not drawn in through the sample gas inlet or through the reference gas inlet. This may be achieved, for example, by arranging the reference gas inlet, the outlet and the sample gas inlet in a manner, such that the main flow directions of the gas drawn through the sample gas inlet, of the gas drawn through the reference gas inlet and/or of the gas blown out through the gas outlet are different. In any case, the gas blown out through the gas outlet should be blown into direction away from the sample gas inlet and the reference gas inlet.

BRIEF DESCRIPTION OF THE DRAWINGS

In the following, examples of the disclosure are discussed with reference to the FIGS. In particular.

DESCRIPTION OF THE INVENTION

Figure 1:
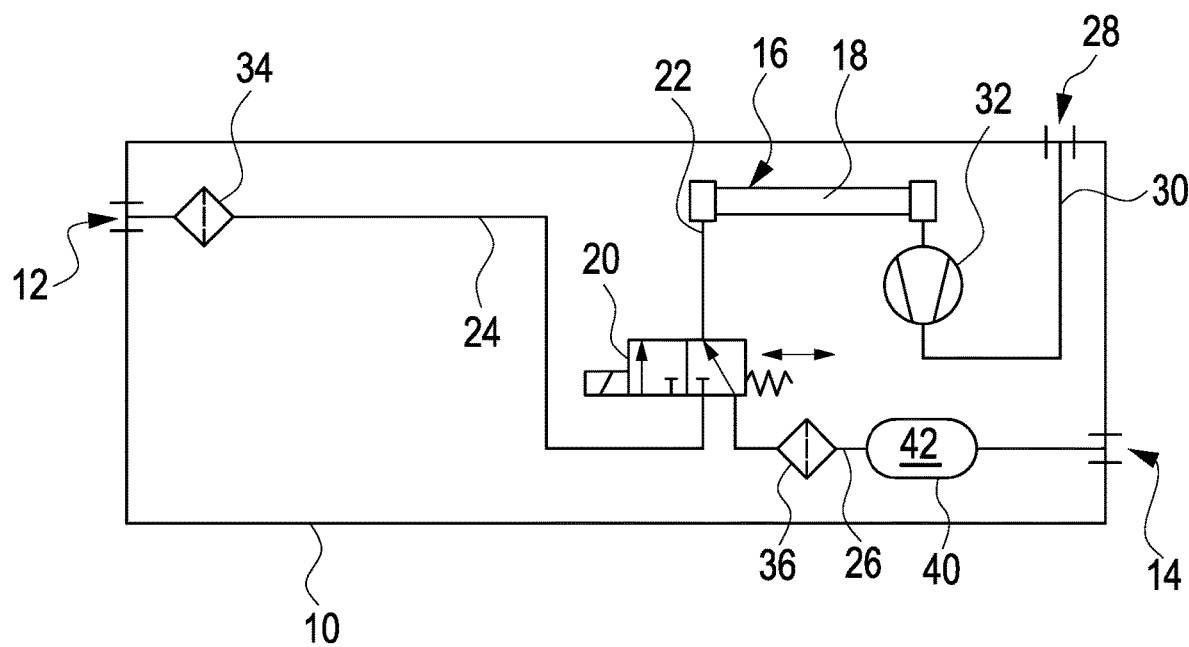
FIG. 1 shows a first embodiment and FIG. 2 shows a second embodiment.

As shown in FIG. 1, the sniffing leak detector 10 generally comprises a sample gas inlet 12 and a reference gas inlet 14. A gas analyzer 16 is of the infrared absorption type with an absorption cuvette 18.

The sniffing leak detector 10 further comprises a switching valve 20 which is connected to the gas analyzer 16 and the cuvette 18 via a first conduit 22. The sample gas inlet 12 is connected to the switching valve 20 via a sample gas conduit 24 and the reference gas inlet 14 is connected to the switching valve 20 via a reference gas conduit 26. The switching valve 20 is adapted to alternatingly switch back and forth between the reference gas inlet 14 and the sample gas inlet 12 by connecting either the sample gas conduit 24 or the reference gas conduit 26 with the first conduit 22 and thus to the gas analyzer 16. Thereby, only the gas sucked in through either the sample gas conduit 12 or the reference gas conduit 14 is con-ducted via the switching valve 20 into the gas analyzer 16 for analysis. The ab-sorption cuvette 18 of the gas analyzer 16 is connected to a gas outlet 28 of the sniffing leak detector 10 via a second conduit 30 which comprises a gas pump 32 generating a continuous flow of gas.

The gas pump 32 can be a vacuum pump adapted to suck gas through either the sample gas inlet 12 or the reference gas inlet 14 and through the gas analyzer 16. As an alternative to the gas pump 32 shown in the figures, the gas pump may be a compressor pump arranged in the gas conduit connecting the switching valve 20 and the gas analyzer 16. This alternative compressor pump is then arranged to press gas drawn in through either the sample gas inlet 12 or the reference gas inlet 14 through the gas analyzer 16 and out of the gas outlet 28.

The sample gas conduit 24 comprises a sample gas filter 34. The reference gas conduit 26 comprises a reference gas filter 36.

The reference gas conduit 26 contains a buffer chamber 40 defining a buffer volume 42. An additional absorber, which is not shown in the FIGS. and through which the gas entering the sniffing leak detector 10 through the reference gas inlet 14 is guided, may be provided. The absorber may be a refrigerant absorber, such as an active carbon filter. The absorber may be provided within the reference gas conduit 26 or within the buffer chamber 40. The absorber additionally stabilizes and homogenizes the target gas concentration within the reference gas.

Figure 2:
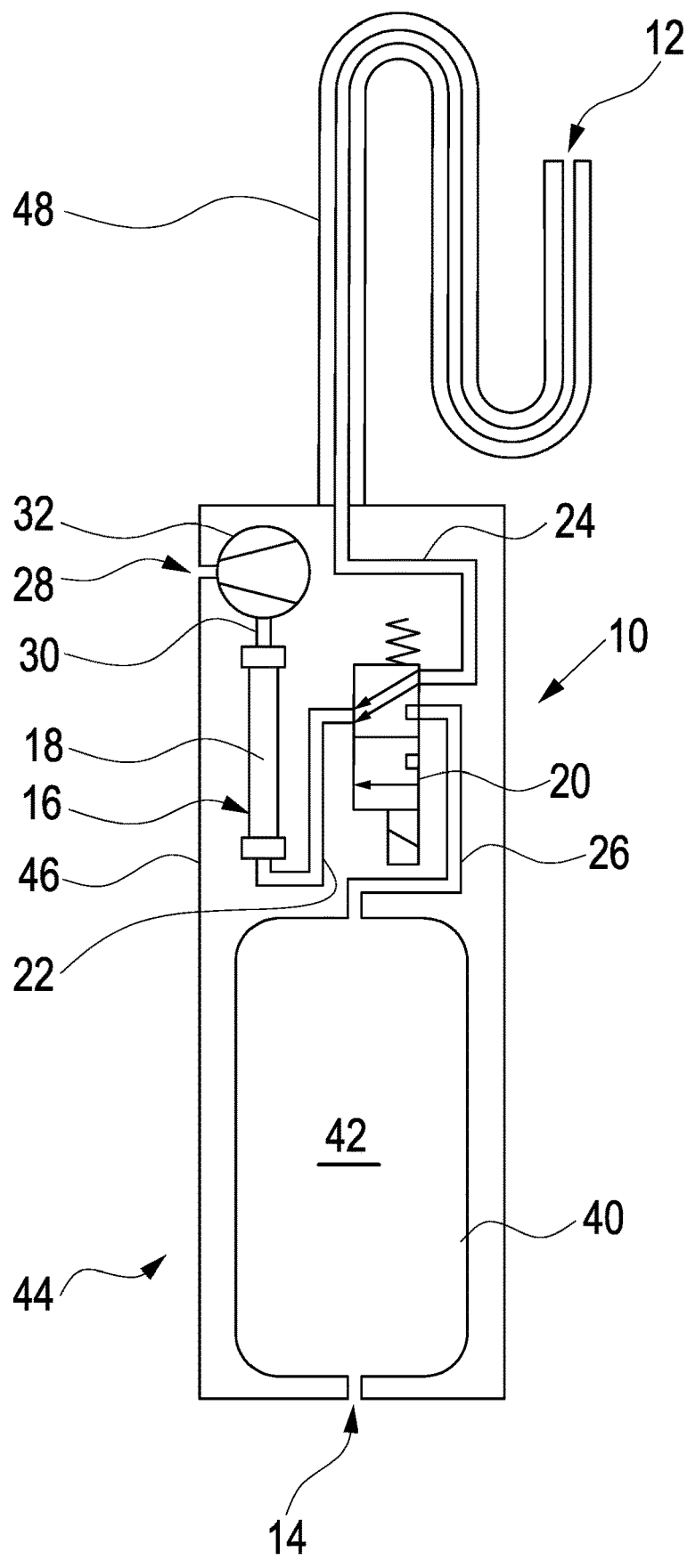

In the embodiment shown in FIG. 2, the sniffing leak detector 10 comprises a hand held device 44 having a housing 46 which is dimensioned to be carried by an operator of the sniffing leak detector 10. The housing 46 houses the buffer chamber 40 and buffer volume 42, the switching valve 20, the gas analyzer 16 and absorption cuvette 18 and the gas pump 32, as well as the sample gas conduit 24, the reference gas conduit 26, the first conduit 22 and the second conduit 30. The reference gas inlet 14 and the gas outlet 28 are formed by openings within the housing 46.

The hand held device 44 comprises a longitudinal and bendable sniffer tip probe 48 which comprises the sample gas inlet 12 at its distal end. The sample gas conduit 24 extends from the sample gas inlet 12 through the sniffer tip probe 48 and into the housing 46. The proximal end of the sniffer tip probe 48 is fixedly attached to the housing 46.

While the sample gas inlet 12 is located at the forward most distal end of the sniffer tip probe 48, the reference gas inlet 14 is located at the rear most proximal end of the housing 46 of the hand held device 44, in order to achieve a maximum distance between the sample gas inlet 12 and the reference gas inlet 14. The gas outlet 28 is located on the side of the housing 46 in a distal portion thereof, such that the distance of the gas outlet 28 to the reference gas inlet 14 and the distance of the gas outlet 28 to the sample gas inlet 12 are almost equal and maximal.

In a further embodiment which is not shown in the Figs., the buffer volume 40 can be arranged in a further housing which is separate from the housing 46 of the hand held device 44. A flexible gas line may connect the housing of the buffer chamber with the housing 46 of the hand held device 44. The separate buffer chamber 40 can, for example, be provided with a handle or belt in order to be carried by an operator. This embodiment allows for a large buffer volume on the one hand, while allowing a small and light hand held device 44 on the other hand.

An even further embodiment which is also not shown in the Figs., comprises the buffer chamber 40 in the form of a room which is separate from the room in which the sample gas inlet 12, the gas analyzer 16 and the switching valve 20 are located. A wall separating these two rooms contains the reference gas inlet 14 in the form of an opening in the wall or, for example, in the form of a slit below or around a connecting door in the wall separating the two rooms.

The invention claimed is:

1. A sniffing leak detector comprising:
   a handheld device with a sniffer tip probe comprising a sample gas inlet;
   a reference gas inlet;
   a gas analyzer; and
   a switching valve adapted to alternatingly connect the sample gas inlet to the gas analyzer and the reference gas inlet to the gas analyzer in a gas conducting manner, such that either a gas drawn through the sample gas inlet or a gas drawn through the reference gas inlet is analyzed by the gas analyzer,
   wherein the reference gas inlet is not arranged on the sniffer tip probe and thereby is located a remote distance from the sample gas inlet,
   wherein the sniffing leak detector comprises a reference gas conduit, which connects the reference gas inlet and the switching valve, and comprises a buffer chamber defining a buffer volume, which permits homogeneous mixing of the gas drawn into the buffer chamber through the reference gas inlet with a remaining gas in the buffer chamber, and
   wherein the buffer chamber comprises a buffer chamber inlet connected to the reference gas inlet and a buffer chamber outlet connected to the switching valve, wherein the buffer chamber outlet is off-set to the buffer chamber inlet with regard to a main gas flow direction through the buffer chamber inlet.

2. The sniffing leak detector according to claim 1, further comprising a vacuum pump adapted to suck gas through either the sample gas inlet or the reference gas inlet, and through the gas analyzer.

3. The sniffing leak detector according to claim 1, further comprising a compressor pump adapted to press gas drawn in through either the sample gas inlet or the reference gas inlet through the gas analyzer.

4. The sniffing leak detector according to claim 1, wherein a ratio of a volume of the buffer chamber and a volume flow per second of the gas drawn through the reference gas inlet is at least 1 and at maximum 10,000.

5. The sniffing leak detector according to claim 1, wherein the buffer chamber is adapted to be carried by a user of the sniffing leak detector, the buffer chamber being a component separate from a hand held device.

6. The sniffing leak detector according to claim 1, further comprising an absorber through which a gas entering through the reference gas inlet is passed.

7. The sniffing leak detector according to claim 1, wherein the buffer chamber is part of a hand held device.

8. The sniffing leak detector according to claim 7, wherein the hand held device is formed by a housing containing the buffer chamber.

9. The sniffing leak detector according to claim 1, further comprising an outlet connecting the gas analyzer to an open atmosphere surrounding the sniffing leak detector, wherein the outlet is arranged such that a gas blown out through the outlet into the atmosphere is not drawn in through the sample gas inlet or the reference gas inlet.

10. The sniffing leak detector according to claim 9, wherein a hand held device comprises the reference gas inlet and the outlet such that a main flow directions of the gas drawn through the sample gas inlet, of a gas drawn through the reference gas inlet and of a gas blown out through the outlet are different.

11. A sniffing leak detector comprising:
a handheld device with a sniffer tip probe comprising a sample gas inlet;
a reference gas inlet;
a gas analyzer; and
a switching valve adapted to alternatingly connect the sample gas inlet to the gas analyzer and the reference gas inlet to the gas analyzer in a gas conducting manner, such that either a gas drawn through the sample gas inlet or a gas drawn through the reference gas inlet is analyzed by the gas analyzer,
wherein the reference gas inlet is not arranged on the sniffer tip probe and thereby is located a remote distance from the sample gas inlet,
wherein the sniffing leak detector comprises a reference gas conduit, which connects the reference gas inlet and the switching valve, and comprises a buffer chamber defining a buffer volume, which permits homogeneous mixing of the gas drawn into the buffer chamber through the reference gas inlet with a remaining gas in the buffer chamber, and
wherein the buffer chamber comprises a swirling mechanism adapted to cause turbulences in a gas stream entering the buffer chamber through the reference gas inlet.

12. A sniffing leak detector comprising:
a handheld device with a sniffer tip probe comprising a sample gas inlet;
a reference gas inlet;
a gas analyzer; and
a switching valve adapted to alternatingly connect the sample gas inlet to the gas analyzer and the reference gas inlet to the gas analyzer in a gas conducting manner, such that either a gas drawn through the sample gas inlet or a gas drawn through the reference gas inlet is analyzed by the gas analyzer,
wherein the reference gas inlet is not arranged on the sniffer tip probe and thereby is located a remote distance from the sample gas inlet,
wherein the sniffing leak detector comprises a reference gas conduit, which connects the reference gas inlet and the switching valve, and comprises a buffer chamber defining a buffer volume, which permits homogeneous mixing of the gas drawn into the buffer chamber through the reference gas inlet with a remaining gas in the buffer chamber, and
wherein the buffer chamber is formed by a first room next to a second room in which the sample gas inlet is located, a wall separating the first room from the second room comprising the reference gas inlet.

* * * * *